United States Patent [19]

D'Arrigo

[11] Patent Number: 5,556,626
[45] Date of Patent: Sep. 17, 1996

[54] ANTINEOPLASTIC DRUG OF PLANT ORIGIN AND PROCESS FOR THE PREPARATION THEREOF

[76] Inventor: Claudio D'Arrigo, 2 Via Elea, I-00183 Rome RM, Italy

[21] Appl. No.: 39,270

[22] PCT Filed: Aug. 25, 1992

[86] PCT No.: PCT/IT92/00106

§ 371 Date: Apr. 21, 1993

§ 102(e) Date: Apr. 21, 1993

[87] PCT Pub. No.: WO93/04689

PCT Pub. Date: Mar. 18, 1993

[30] Foreign Application Priority Data

Aug. 28, 1991 [IT] Italy .................... RM91A0637

[51] Int. Cl.⁶ .................................................. A61K 35/78
[52] U.S. Cl. ........................................ 424/195.1; 514/783
[58] Field of Search ............................ 424/195.1

[56] References Cited

PUBLICATIONS

*Index of Garden Plants* Ed. Mark Griffiths, pp. 832–833, (The MacMillan Press Ltd.), 1994.

M. I. Fernandez, et al. Constituents of a Hexane Extract, Phoenix *Actylifera*, Phytochemistry, 22(9) 2087–8, 1983.

*Primary Examiner*—John Kight
*Assistant Examiner*—Howard C. Lee
*Attorney, Agent, or Firm*—Birch, Stewart, Kolasch & Birch, LLP

[57] ABSTRACT

Provided are active principles having an antitumoral activity, extracted from plants of the family Palma, the subfamily Phoenicoideae and the genus Phoenix, and pharmaceutical preparations containing at least one of the substances and compositions present in said extracts. In comparison with all the other antitumoral drugs known to date, these active principles show increased selectivity on neoplastic cells and a lower involvement of the normal cells. Also provided is a process for extraction and separation of the components of the extracts, and their use for the preparation of antineoplastic drugs and drugs for the treatment of other pathologies.

27 Claims, No Drawings

ANTINEOPLASTIC DRUG OF PLANT ORIGIN AND PROCESS FOR THE PREPARATION THEREOF

The present invention relates to a new chemotherapeutic drug having antineoplastic activity, extracted from the fruits of plants of the family Palma, the subfamily Phoenicoideae and the genus Phoenix.

In research aimed at the fight against cancer, one of the most representative lines of research is that of antitumoral chemotherapy. The antineoplastic chemotherapeutic agents isolated up to date have the widest of origins and chemical characteristics. Certain of these antiproliferative agents are extracted from plants, such as, for example, colchicine from *Colchicum autumnale* and vincaleucoblastin from *Vinca rosea*. However, all these substances, along with a certain specifically antitumoral activity, show a low selectivity with respect to the degenerated cells; for this reason their interference on the metabolism of healthy cells represents a large obstacle to their indiscriminate use.

The present inventor has already patented another antitumoral drug of plant nature (and more particularly the substance CIDI extracted from the fruit of *Pittosporum tobira*), prossessing highly selective antitumoral activity and a toxicity level greatly reduced with respect to all the other antineoplastic drugs. Continuing along this line of research, the present inventor has isolated a new antineoplastic chemotherapeutic agent, once again of plant origin, which also shows highly selective antitumoral activity and extremely low toxicity.

A first object of the present invention is therefore a process for obtaining substances and/or compositions having antineoplastic activity, characterized by the fact that parts and/or products of plants belonging to the family Palma—at whatever stage of their development and maturity—are subjected essentially to the following operations:

a) extraction of components by maceration in an organic solvent;

b) optional stirring and shaking of the solution containing the extract with another solvent at least partially miscible with the first, to divide the components of the extract in the phases which form;

c) optional treatment of each phase, independently one from the other, using at least one or two organic liquids having solvent activity with respect to at least one of the components of the extract, followed by filtering of any precipitate which forms and evaporation to a dry state of the floating residue;

d) optional separation of the components found in each liquid phase; and e) collection of the separated components having antineoplastic activity and of those without antineoplastic activity.

The extracts can be brought to a dry state and purified before each successive stage of the process.

The plants of the family Palma are preferably of the subfamily Phoenicoideae and the genus Phoenix. In this regard, the plants can be selected, for example, from numerous species including *Phoenix canadiensis, Phoenix dactylifera, Chamaerops excelsa, Chamaerops humilis* and many others.

The solvent can be an alcohol. Good results have been obtained using ethyl alcohol.

The volume ratio between organic solvent and parts of plants to be treated is preferably between 1:10 and 10:1.

The treatment times are preferably between 5 minutes and 3 months. The treatment temperatures can vary, preferably between 5° C. and 100° C.

The total alcoholic extract of the drug, at a dilution of 1 mg/ml, can be analyzed on an HPLC (Perkin-Elmer series 250 liquid chromatograph), using a 125 mm–4 mm RP 18 column with a methanol-$H_2O$ (80:20) mobile phase and wavelengths equal to 210 nm. Said total alcoholic extract shows approximately 14 peaks with RT of from 1.123 (1st peak) to 33.461 (14th peak); the most representative peaks are of RT 1,123 (3.36% area); RT 1.301 (3.01% area); RT 1.583 (63.34% area); RT 2.133 (14.88% area) and RT 2.636 (3.33% area).

Separation of the components of the extract can preferably be carried out chromatographically. Good results have been obtained using chromatography on a silica gel column or on an HPLC preparative column.

Extraction can be performed using methanol and collecting the components which have HPLC retention times of about 1.123, 1.301, 1.583, 2.133 and 2.636.

After extraction with ethanol, the solution obtained can be shaken with chloroform, forming two phases, an alcohol-chloroform phase of a green color, and an aqueous phase of bordeaux-red color. In this case the components having antineoplastic activity are found in the aqueous phase.

The aqueous solution can be concentrated by evaporation in a rotavapor and, at this point:

1) ethyl alcohol can be added to the flask, forming a suspension; after this, petroleum ether can then be added which, after stirring, gives rise to the formation of a large precipitate which, once it has been resolubilzed in ethanol-water and concentrated to approximately 30 ml, is suspended in isopropyl alcohol and then dried out. The floating portion can in turn be evaporated and dried out, giving rise to the formation of a red amorphous substance; finally, this substance can be crystallized if, after being solubilized in a little methanol, it is dried out after addition of isopropyl alcohol, which causes an extremely fine suspension to form;

2) or preferably, after having concentrated the aqueous solution, methyl alcohol can be added to the flask, forming a suspension; after this, ethyl ether can be added which, after stirring, causes the formation of a large, flaky precipitate; after removing the floating portion, the precipitate is suspended in isopropyl alcohol and dried out in rotavapor, causing the formation of a light rose-pink powder.

The invention also relates to substances and compositions per se, characterized in that they can be obtained using the process described above.

The present invention has also as its subject substances and compositions having antineoplastic activity, characterized in that they can be obtained using the process indicated above.

The substances and compositions having antineoplastic activity can be treated to take on the form of salts, compounds or complexes, in order to make them water soluble.

A further subject of the present invention is a pharmaceutical preparation, characterized in that it contains as at least one of its active principles a substance or composition selected from the group of substances or compositions having antineoplastic activity, which can be obtained using the process described above, or combinations thereof.

The pharmaceutical preparation can be chosen from the group comprising aqueous solutions for parenteral use, capsules for oral use, suppositories for rectal use, ovules for vaginal use, unguents, ointments, creams and gels.

The aqueous solution can be packed in vials. Each vial contains from 0.5 to 2.5 g of active principle, preferably between 1.2 and 1.7 g of active principle.

In the case of a pharmaceutical preparation in the form of capsules, each capsule contains 0.1–2 g of active principle, preferably 0.8–1.2 g of active principle.

In the case of a pharmaceutical preparation in the form of suppositories for rectal use, each suppository contains from 0.5 to 2.5 g of active principle, preferably from 1.2 to 1.7 g of active principle.

In the case of a pharmaceutical preparation in the form of globuli for vaginal use, each globulus contains from 0.5 to 2.5 g of active principle, preferably from 1.2 to 1.7 g of active principle.

In the case of a pharmaceutical preparation in the form of an unguent, ointment, cream or gel, the excipient for topical use contains between 0.5 and 12% of active principle, preferably from 3 to 7% of active principle.

The present invention also relates to the use of components obtained using the above extraction, separation and collection process, alone or in combination, for the preparation of drugs for the treatment of pathologies other than neoplastic ones.

Up to this point, a general description has been given of the present invention. With the help of the following examples, a more detailed description will now be provided to give greater clarification of the objects, characteristics, advantages and working methods of the invention.

EXAMPLE 1

Method for the extraction and purification of the active principles

A certain amount of fruits of Chamaerops excelsa are set to infuse at room temperature with a quantity of 95% ethyl alcohol sufficient to cover the fruits (approximately 1:1 by volume, approximately 7:1 by weight). They are left to macerate for at least 30 days, and then filtered. 500 ml of alcoholic extract obtained as described above are poured into a separatory funnel along with an identical amount of chloroform. After stirring a number of times, separation occurs, which is completed after 24 hours; in the lower part of the funnel an alcohol-chloroform solution of a green color separates; in the upper part an aqueous solution of a bordeaux-red color (Red soluble fraction=RSF) formed by the water soluble substances extracted from the water initially present in the fruit forms. RSF is present at approximately 20% of the volume, and is formed almost exclusively of components which, by HPLC, have RTs of 1.175 (22,04% area), 1.575 (67.47% area) and 2.284 (10.49% area). The substance RSF, when dried out, is made up of an amorphous substance of a red color. The alcohol-chloroform solution of a green color (insoluble green fraction=IGF) which separates off into the lower part of the separatory funnel, when dried out, is insoluble in $H_{20}$ and, when solubilized in methanol, shows 4 peaks by HPLC with RTs of: 1,089 (14.17% area); and 1.299 (8.29% area); 1.600 (68.10% area); 2.268 (9.43% area).

EXAMPLE 2

Methods for purification of the active principle

1) First method.

The aqueous solution (RSF) remaining after the operations performed in Example 1 (made up of the total alcoholic extract less IGF), is greatly concentrated by evaporation in a flask in a rotavapor at 45° C., bringing it down to a volume of approximately 30 ml. At this point, 300 ml of ethyl alcohol are added to the flask. A suspension forms. An equal volume (300 ml) of petroleum ether is added. The mixture is stirred. A large precipitate forms. The limpid floating portion is collected, filtered and dried out in a rotavapor. An amorphous substance is obtained, red in color, which is soluble in $H_2O$.

The red amorphous substance is solubilized in methanol and concentrated a number of times in a rotavapor until a strongly concentrated, completely methanolic solution is obtained. At this point isopropyl alcohol (approximately 200 ml) is introduced into the flsk, causing the formation of an extremely fine suspension. This is dried out. An extremely fine powder is thus obtained, of a rose-pink color, which is, in fact, purified and crystallized RSF.

The RSF powder is soluble in $H_2O$, methanol and ethanol; insoluble in isopropyl alcohol. Its solutions take on a brilliant red color.

The RSF powder, solubilized in methyl alcohol and examined by HPLC using the usual method, shows a single peak with a RT equal to 1.591.

The RSF powder is extremely hygroscopic and, after resting in a vacuum dryer, should be conserved in sealed bottles under vacuum.

Separately, the precipitate which formed in the flask is also solubilized in ethyl alcohol-$H_2O$ (3:1) and concentrated by evaporation in a rotavapor according to the usual method until reaching a volume of approximately 30 ml. At this point isopropyl alcohol is added to the flask, forming a fine suspension, and the whole is dried out. A pale rose-pink powder is obtained, showing the same RT by HPLC as described in point a) of the second method.

2) Second method.

The aqueous solution (RSF) remaining after the operations performed in Example 1 (made up of the total alcoholic extract less IGF), is evaporated in a flask in a rotavapor at 45° C., bringing it down to a volume of 30 ml.

At this point, 300 ml of methyl alcohol are added to the flask. A fine suspension forms. The mixture is stirred. An equal volume of ethyl ether is added. The mixture is stirred. A consistant large, flaky precipitate forms. The floating portion is removed. All the precipitation operations described in point 2 up to now, can be repeated a number of times, in order to obtain an increasingly pure active principle.

Having removed the floating portion, the precipitate is suspended in approximately 100 ml of isopropyl alcohol, and then dried out in a rotavapor. A fine powder of a rose-pink color is thus obtained, which will hereinafter be called DEGU.

The DEGU powder is insoluble in acetone, benzene, chloroform, ethyl ether, petroleum ether, ethyl alcohol, methyl alcohol, isopropyl alcohol; it is soluble in $H_2O$.

Chemical and chemical-physical characteristics

DEGU powder from a single precipitation:
a) HPLC.

Column RP 18 125 mm. 4 mm, mobile phase methanol-water (80:20), wavelength 210 nm, concentration 1 mg/ml: RT 0.728 (2.18% area); RT 0.994 (40.89% area); RT 1.452 (56.93% by area).

Same method, concentration 2 mg/ml; RT 1.031 (40.75% area); RT 1.457 (59.26% area).

Spherical column Supelcosil LC-$NH_2$ 5 u, mobile phase $CH_3CN$-$H_2O$ (3:1), flow 1.5 ml/min., UV detector 217 nm: RT 1.702 (conc. 15.823); RT 1.958 (conc. 75.7988); RT 5.039 (conc. 9.1218).

Irregular Chrompack Lichrosorb RP 18–10 u column, mobile phase $CH_3CN$-$H_2O$ (3:1), flow 1,5 ml/min., UV detector at 217 nm: RT 1.503 (conc. 15.3867); RT 1.826 (conc. 42.5747); RT 2.019 (conc. 38.1984); RT 4.132 (conc. 3.8399).

b) IR Spectrum (Spectrophotomenter IR Perkin Elmer Mod. 683) in KBr medium, concentration 1 mg/100 mg.

Observable bands:

| | | |
|---|---|---|
| 3350 $cm^{-1}$ | stretching | OH associated |
| 2900 $cm^{-1}$ | stretching | $CH_3$ and $CH_2$ |
| 1600 $cm^{-1}$ | stretching | C=C |
| 1510 $cm^{-1}$ | bending | OH associated |
| 1400 $cm^{-1}$ | bending | CH |
| 1380 $cm^{-1}$ | bending | $CH_3$ |
| 1250 $cm^{-1}$ | bending | free OH |
| 1050 $cm^{-1}$ | stretching | C—O | c) UV Spectrum (Spectrophotometer UV-vis Perkin Elmer Mod. Lambda 5).

Solution in $CH_3CN$-$H_2O$ (4:1), concentration $5 \times 10^{-2}$ mg/ml:

maximum absorption: principal at 204 nm secondary at 279 nm

Solution in $CH_3OH$-$H_2O$ (3:1), concentration $5 \times 10^{-2}$ mg/ml:

maximum absorption: principal at 202 nm secondary at 279.5 nm d) NMR Spectra.

NMR spectra determined using a Bruker AC apparatus at 200 MHz (proton) and 50 MHz (carbon). The samples were prepared by dissolving 55 mg of substance in 0.6 ml of DMSO-$d_6$ with the addition of 15 mg of the sodium salt of 3-(trimethylsilyl)propanesulfonic acid (DSS) as an internal standard.

For the $^1H$ spectrum, 3668 transients were accumulated using a 30° impulse. Exchange of mobile protons was carried out by means of addition to the sample of 5 drops of $D_2O$, and the relative $^1H$ spectrum was determined by accumulating 212 transients.

The $^{13}C$ spectrum was determined accumulating 11,565 transients, using a 90° impulse followed by a delay of 1.4 seconds.

From examination of the proton spectra, numerous signals can be noted in the area comprised between 2.5 and 4 ppm (due probably to C-H of alcoholic or etheric type); there is also the presence of mobile protons, of probable hydroxylic nature, in the area comprised between 4 and 5 ppm. In the spectra there are also weak signals in the vinylic proton area.

The $^{13}C$ spectrum provides similar information, showing some peaks in the vinylic carbon area and numerous signals in the alcoholic and etheric carbon area.

| e) | Elemental analysis: | C % | 38.48 |
|---|---|---|---|
| | | H % | 5.72 |
| | | N % | — |
| | | O % | 55.80 |

Minimal empirical formula closest to the above analysis: $C_9H_{16}O_{10}$.

f) Melting point: 95°–130° C. (dec.).

g) pH of the aqueous solution: 6.05.

The above mentioned chemical and chemical-physical characteristics of the substance DEGU can suffer variation according to the degree of purification effected (N° of precipitations or washings), as summarized in the following table:

| Method | RSF in toto (Example 1) | Powder derived from 1st washing | Powder derived from 2nd washing | Powder derived from 3rd washing |
|---|---|---|---|---|
| Weight of dry substance in g/l | ~26 | ~12 | ~8 | ~5 |
| m.p. (dec.) | 70°–75° C. | 95°–130° C. | 130°–150° C. | 170°–200° C. |
| HPLC (RT) (col. RP18, mobile phase methanol-$H_2O$ 80:20, lambda 210 nm, conc. 1 mg/ml) | 1.175 (22.4%) | 0.728 (2.18%) | 0.088 (0.36%) | 0.777 (0.99%) |
| | 1.575 (67.47%) | 0.994 (40.89%) | 1.085 (77.78%) | 1.044 (41.41%) |
| | 2.284 (10.49%) | 1.452 (56.93%) | 1.579 (21.86%) | 1.571 (11.51%) |
| | — | — | — | 2.438 (46.09%) |
| pH aqueous solution | 6.2 | 6.05 | 6.55 | 6.41 |
| $LD_{50}$ to mice Swiss per i.p. mg/kg | >2000 | >2000 | >2000 | >2000 |

EXAMPLE 3

Method of chromatographic separation of the active principles

The total alcoholic extract of the drug is dried out in a rotavapor and resolubilized in a small amount of methanol and water. Using this solution, chromatographic separation is carried out both on a silica-gel 60 column and on an HLPC preparative column. Pure fractions are thus obtained which, as stated above, correspond to peaks with RTs of: 1.123; 1.301; 1.583; 2.133 and 2.636.

EXAMPLE 4

Tests demonstrating the antineoplastic activity both in vitro and in vivo.

The substances and/or compositions obtained according to the previous examples, soluble or solubilized using ethyl alcohol in water, show a marked antineoplastic activity, together with acceptable toxicity and the absence of immunosuppressive activity. These peculiar characteristics had already been observed by the author of the present invention in active principles isolated from another plant which, as stated above, formed the object of a previous patent: this is probably due to the fact that this group of substances has above all a lytic activity on all the membranes of the neoplastic cell, from the parietal membrane to those of the various cytoplasmatic organelles, to the nuclear membrane.

The notable selective antineoplastic activity on tumoral cells is demonstrated, at a histological level, both in vitro and in vivo, by evident alterations to the tumoral cells, which appear to increase in volume, conglutinate, show extroversion and fraying of the cell membrane, and an extremely vacuolated and frothy cytoplasm with hypochromia of the nuclear chromatin and pale nucleoles. Demonstration of the high selectivity of these substances is shown by the fact that all the lesions listed above are completely lacking in normal cells undergoing similar treatment.

In vivo, antineoplastic activity of the substances mentioned above was tested on Sa 180 of Swiss mouse, generally using a dose of between 20 and 1000 mg/Kg/day, according to the substance used, given intraperitoneally for 8 consecutive days, starting from the day following the transplant. Compared with an average survival time of 23.0 days in the control animals, rejection of the tumor was seen in 80% of the treated animals, which can therefore be considered as definite survivors.

A single subcutaneous injection, given 24 hours after transplant of the tumor, at a dose eight times that of the single intraperitoneal injection, is capable of causing rejection of the tumor in 100% of cases.

For therapeutic application, the substances according to the present invention, and their salts, compounds or complexes, are preferably used in the form of an aqueous solution for intramuscular, endovenous or endocavitary injections.

I claim:

1. A process for producing an antineoplastic substance comprising:
   (a) macerating and extracting a fruit of the species *Phoenix canadiensis, Phoenix dactylifera, Chamaerops excelsa* or *Chamaerops humilis* of the family Palma, in an alcohol to produce an alcoholic extract;
   (b) stirring or shaking said alcoholic extract of step (a) with chloroform to produce an alcohol-chloroform phase and an aqueous phase;
   (c) concentrating said aqueous phase of step (b) by evaporation to produce a concentrated aqueous phase; then either
   (d) adding ethyl alcohol to said concentrated aqueous phase of step (c) to form a suspension;
   (e) adding petroleum ether to said suspension of step (d) with stirring to produce a precipitate having a limpid floating portion and a remaining portion;
   (f) collecting, filtering, and drying said limpid floating portion of said precipitate of step (e) to obtain an amorphous substance;
   (g) solubilizing and concentrating said amorphous substance of step (f) in methanol until a concentrated methanolic solution is obtained;
   (h) adding isopropyl alcohol to said concentrated methanolic solution to produce a fine suspension; and
   (i) drying said fine suspension to produce a powder;
or
   (m) adding methyl alcohol to said concentrated aqueous phase of step (c) to produce a fine suspension;
   (n) stirring said fine suspension of step (m) and adding an equal volume of ethyl ether to produce a large, flaky precipitate having a floating portion;
   (o) removing said floating portion of said large, flaky precipitate of step (n) to obtain a remaining portion of said large flaky precipitate;
   (p) suspending the remaining portion of said large, flaky precipitate of step (o) in isopropyl alcohol; and
   (q) drying said remaining portion of said large, flaky precipitate of step (p) to produce said antineoplastic substance.

2. The process according to claim 1, wherein said alcohol of step (a) is ethanol.

3. The process according to claim 1, wherein the volume ratio of said alcohol and said fruit of step (a) is between 1:10 and 10:1.

4. The process according to claim 1, wherein step (a) is carried out for an extraction time of 5 minutes to 3 months.

5. The process according to claim 1, wherein step (a) is carried out at a temperature between 5° C. and 100° C.

6. The process according to claim 1, wherein said alcohol of step (a) is ethanol, and said alcoholic extract of step (a) is shaken with chloroform to obtain an alcohol-chloroform phase of a green color and an aqueous phase of a bordeaux-red color in step (b), wherein said antineoplastic substance is present in said bordeaux-red aqueous phase.

7. The process according to claim 6, wherein said aqueous phase is concentrated by evaporation in a flask in a rotavapor in step (c), and said remaining portion of said precipitate of step (e) is evaporated until dry to obtain a pale pink powder, while said limpid floating portion of step (e) is evaporated to obtain an amorphous red substance in step (f).

8. The process according to claim 7, wherein both said pale pink powder and said amorphous red substance are crystallized in the form of a red powder, after suspension in methyl alcohol and isopropyl alcohol.

9. The process according to claim 6, wherein said aqueous phase is concentrated in an evaporation flask in step (c), and said remaining portion of said large, flaky precipitate suspended in isopropyl alcohol in step (p) is dried to obtain a pale rose-pink-colored powder in step (q).

10. An antineoplastic substance produced by the process according to claim 1.

11. The antineoplastic substance according to claim 10, in a form selected from the group consisting of a salt, a compound, a complex and a combination thereof.

12. A pharmaceutical preparation comprising an antineoplastic substance produced by the process according to claim 1 and a pharmaceutically acceptable carrier or excipient.

13. The pharmaceutical preparation according to claim 12, prepared in the form of an aqueous solution for parenteral use.

14. The pharmaceutical preparation according to claim 12, prepared in the form of capsules for oral use.

15. The pharmaceutical preparation according to claim 12, prepared in the form of suppositories for rectal use.

16. The pharmaceutical preparation according to claim 12, prepared in the form of ovules for vaginal use.

17. The pharmaceutical preparation according to claim 12, prepared in the form of an unguent, ointment, cream or gel.

18. The pharmaceutical preparation according to claim 13, prepared in vials, each vial containing between 0.5 and 2.5 g of said antineoplastic substance.

19. The pharmaceutical preparation according to claim 18, in which each vial contains between 1.2 and 1.7 g of said antineoplastic substance.

20. The pharmaceutical preparation according to claim 14, prepared in the form of a capsule, each capsule containing 0.1–2.0 g of said antineoplastic substance.

21. The pharmaceutical preparation according to claim 20, in which each capsule contains from 0.8 to 1.2 g of said antineoplastic substance.

22. The pharmaceutical preparation according to claim 15, prepared in the form of a suppository for rectal use, each suppository containing from 0.5 to 2.5 g of said antineoplastic substance.

23. The pharmaceutical preparation according to claim 22, in which each suppository contains from 1.2 to 1.7 g of said antineoplastic substance.

24. The pharmaceutical preparation according to claim 16, prepared in the form of an ovule for vaginal use, each ovule containing from 0.5 to 2.5 g of said antineoplastic substance.

25. The pharmaceutical preparation according to claim 24, in which each ovule contains from 1.2 to 1.7 g of said antineoplastic substance.

26. The pharmaceutical preparation according to claim 17, prepared in the form of an unguent, ointment, cream or gel, with an excipient for topical use containing between 1.5 and 12% of said antineoplastic substance.

27. The pharmaceutical preparation according to claim 26, wherein said excipient for topical use contains between 3 and 7% by weight of said antineoplastic substance.

* * * * *